United States Patent [19]

Okrongly et al.

[11] Patent Number: 5,286,789

[45] Date of Patent: Feb. 15, 1994

[54] SOLID PHASE MULTIPLE PEPTIDE SYNTHESIS

[75] Inventors: David Okrongly, Sunnyvale; Brian R. Clark, Redwood City, both of Calif.; Jack Spesard, Arlington Heights, Ill.

[73] Assignee: Applied Immune Sciences, Inc., Santa Clara, Calif.

[21] Appl. No.: 41,901

[22] Filed: Apr. 2, 1993

Related U.S. Application Data

[63] Continuation of Ser. No. 671,671, Mar. 19, 1991, abandoned, which is a continuation of Ser. No. 357,987, May 26, 1989, abandoned.

[51] Int. Cl.$^5$ .................... C08F 8/32; C08L 89/00
[52] U.S. Cl. ................. 525/54.11; 525/54.1; 525/333.6; 525/350; 525/374; 525/379; 530/333; 530/334; 530/335; 530/815; 530/816
[58] Field of Search ............. 525/54.1, 54.11, 333.6; 530/333, 334, 335

[56] References Cited

U.S. PATENT DOCUMENTS

| | | | |
|---|---|---|---|
| 3,875,114 | 4/1975 | Swiger | 525/333.6 |
| 3,906,031 | 9/1975 | Carpino | 930/10 |
| 4,315,998 | 2/1982 | Neckers et al. | 525/332 |
| 4,914,151 | 4/1990 | Mergler | 525/54.1 |
| 4,933,410 | 6/1990 | Okrongly | 525/333.6 |
| 4,978,724 | 12/1990 | Clark | 525/350 |
| 5,241,012 | 8/1993 | Clark | 525/333.6 |

FOREIGN PATENT DOCUMENTS

| | | |
|---|---|---|
| 273895 | 7/1988 | European Pat. Off. |
| 294059 | 12/1988 | European Pat. Off. |
| WO84/03506 | 9/1984 | PCT Int'l Appl. |
| WO84/03564 | 9/1984 | PCT Int'l Appl. |
| WO86/00991 | 2/1986 | PCT Int'l Appl. |

OTHER PUBLICATIONS

Organic Chemistry 3rd Ed., Morrison & Boyd Allyn & Bacon (1973) pp. 456–457.
Merrifield, Solid Phase Synthesis 24 Agew. Chem. (Oct. 1985) at 749–892.
Giralt et al. (Par Resin) A New Polymeric Support . . . 37(10) Tetrahedron (1981) At 2007–10.
Jakubke, et al., Aminosauren, Peptide Proteine, (1982) Chapter 2.2.7, pp. 204–212, Verlag Chemie, Weinheim, Germany.
Nakagawa et al., "Synthesis of protected peptide segments and their assembly on a polymer-bound oxime: application to the synthesis of a peptide model for plasma apolipoprotein A-I," Chem. Abstracts, 98(13):107756b.
Mergler et al., "Peptide synthesis by a combination of solid-phase and solution methods. I. A new very acid-labile anchor group for the solid phase synthesis of fully protected fragments," Chem. Abstract, 110(11):95779n.
Shekhani et al., "Carboramidomethyl esters as useful handle in polystyrene-based peptide synthesis: cleavage of peptide with mercaptide," Tetrahedron Letters, 31(3):339–340 (1990).

Primary Examiner—Joseph L. Schofer
Assistant Examiner—Fred Zitomer
Attorney, Agent, or Firm—Morrison & Foerster

[57] ABSTRACT

Methods and compositions are provided, where oligopeptides are produced on a transparent surface while retaining transparency by the cyclical addition of protected monomers. Reagents are specifically selected to allow for efficient reproducible addition, while maintaining transparency of the support. Linkers are provided which permit retention of the oligopeptide to the surface or release of the oligopeptide at completion of the preparation of the oligopeptide. The oligopeptide bound to the support finds use in diagnostic assays, as well as other application, while the free oligopeptides may be used in a variety of ways.

26 Claims, No Drawings

SOLID PHASE MULTIPLE PEPTIDE SYNTHESIS

This application is a continuation of application Ser. No. 07/671,671, filed Mar. 19, 1991, which is a continuation of 07/357,987, filed May 26, 1989 (now abandoned).

INTRODUCTION

1. Technical Field

The field of the subject invention concerns peptide synthesis on a solid support.

2. Background

The investigation of biological processes has greatly expanded with the advent of cloning, sequencing, restriction enzymes, gene banks, improved diagnostic equipment, as well as many other advances which have allowed for the increasing ability to investigate the mechanisms of physiological processes and the molecules involved with such processes. As increasing numbers of biological molecules are isolated and characterized, there has been a concomitant interest in the preparation of peptides. In many. physiological processes, oligopeptides play a central role in the process. This is exemplified by the interaction between antigen presenting cells, such as macrophage and B-cells, with T-cells, where the oligopeptide must bind to the MHC antigen and be recognized by the T-cell receptor in conjunction with MHC antigen. Even where the whole protein plays a role, frequently only a small sequence of the protein can mimic a substantial proportion of the activity of the intact protein. Thus, epitopic sites which bind to immunoglobulins may be used for binding to the antibodies, as haptens to induce antibody formation or may be used in diagnostic assays for detecting proteins or their complementary receptors. Peptides may also play a significant role in screening for compounds which may be active as drugs or may provide for insights in the conformation required for agonist or antagonist activity. The preparation of a series of oligopeptides may also serve to define the binding site of receptors and the effect of transduction of signals as a result of changes in sequence.

There is, therefore, substantial interest in methods which provide for simple and efficient techniques for the production of a variety of oligopeptides of different composition.

3. Relevant Literature

PCT applications WO84/03564, WO84/03506, and WO86/00991 provide techniques for the production of a plurality of peptides. See also the references cited therein. Co-pending application Ser. No. 051,917, filed May 19, 1987, describes methods for functionalizing polystyrene surfaces.

SUMMARY OF THE INVENTION

Functionalized polystyrene surfaces having an active displaceable halide or pseudohalide are substituted with an aminoalkyl or hydroxyalkyl chain as a linker. The resulting linking group is then reacted with an appropriately protected amino acid activated ester, followed by deprotection and extension with additional protected amino acids. Optionally, the linker may be further extended with a benzyl alcohol group. Linkers employing the hydroxyl group are first reacted with a carboxyl functionality more reactive than a pentafluorophenyl activated ester, e.g. symmetric anhydride, where subsequent amino acids are added as the pentafluorophenyl or the like activated ester.

DESCRIPTION OF SPECIFIC EMBODIMENTS

Methods and compositions are provided for producing efficiently and rapidly, usually substantially concurrently, a plurality of oligopeptides with a high order of fidelity. The method employs an activated polystyrene surface terminating in an amino or hydroxyl group. The oligopeptide is then prepared by sequentially adding activated carboxyl protected amino acids employing specific reagents for the coupling and deprotection in each cycle.

The first stage of the process is the activation of polystyrene. The polystyrene may be present in a variety of forms, such as multiwell plates, rods, sheets, beads, substantially closed or open containers, flasks, where specific areas on the sheet may be dimpled, separated by raised lines or other barriers, or the like. Desirably, the polystyrene is fabricated, e.g. extruded or molded where rods may be chopped to provide beads. The characteristics of the device are that it will allow for the simultaneous manipulation at a plurality of sites of the sequential addition of the same or different amino acids and the same or different reagents for each cycle of addition.

The functionalization is extensively described in U.S. Pat. No. 4,933,410 filed Mar. 29, 1989. In this method, an α-hydroxyalkyl-2-substituted-acetamide is employed where the substituent is a halide or pseudohalide. For the most part, the polystyrene objects which are activated, will be primarily non-crosslinked, usually having fewer than about 0.5 percent crosslinks, more usually fewer than about 0.1 percent crosslinks. The polystyrene products are normally fabricated, molded, or extruded so as to provide for a smooth surface with few indentations or canyons. With these products, molecules may be bound to the surface and be readily available for binding to other molecules. By employing the subject process with the molded or extruded polystyrene, the polystyrene remains substantially transparent, so that the progress of the reaction may be monitored.

Retention of the desirable properties of the fabricated polystyrene is achieved using functionalized Y-methyl acetamides, where the Y-methyl group reacts with the polystyrene in a polystyrene non-swelling or non-dissolving solvent in the presence of a Lewis acid catalyst under mild conditions, and Y is a moiety capable of undergoing nucleophilic substitution by an aryl group, e.g. benzene in the presence of a Lewis acid catalyst. The α-acyl functional group of the Y-methyl amide is a group which is stable under the aromatic electrophilic substitution conditions, but can be readily displaced by a Lewis base under nucleophilic substitution conditions.

The compounds used for functionalizing the polystyrene will for the most part have the following formula

wherein:

R is an alkyl group of from 1 to 3, more usually from 1 to 2 carbon atoms or hydrogen, usually hydrogen;

X is a halogen (including pseudohalogen), where the halogen is of atomic number of at least 17, wherein X may be chlorine, bromine, or iodine, or a pseudohalogen, such as arylsulfonate esters, sulfonium salts, or the like. Usually, when other than halogen, the substituent on the α-carbon atom of the acyl group will be of at least about 2 carbon atoms and not more than about 10 carbon atoms, usually not more than about 8 carbon atoms, and may have from 1 to 6, more usually from 1 to 5, and preferably from 1 to 4 heteroatoms, which include halogen and chalcogen (oxygen and sulfur), where any counterion is not included in the limitations. While many other functional groups may be present, such as cyano and nitro, for the most part they do not play a useful role and the compounds are not generally available.

Y may be the same or different from X, usually different, and is a group capable of nucleophilic substitution, particularly oxy-derivatives, halides and pseudohalides, where the oxy-derivatives may be esters, either organic or inorganic, or ethers. Y will usually be of not more than 20 carbon atoms, usually not more than 12 carbon atoms, and up to about 8 heteroatoms, usually not more than about 6 heteroatoms. Y groups include hydroxy, halogen of atomic number of at least 17, pseudohalides such as arylsulfonate esters, esters such as phosphates, carboxylates, imidates, etc, ethers, such as alkyl, aryl, oxyalkyl, etc.

N-hydroxymethyl acetamides which find use are the 2-substituted N-hydroxymethyl acetamides, including but not limited to N-(hydroxymethyl) 2-chloroacetamide, N-(hydroxymethyl) 2-bromoacetamide, N-(hydroxymethyl)-2-iodoacetamide, N-(hydroxymethyl), O-(pbromobenzenesulfonyl) glycolamide, N-(hydroxymethyl), O-(p-toluenesulfonyl) glycolamide, N-(hydroxymethyl)-2-acetamidopentamethylenesulfonium iodide, and N-(hydroxymethyl) 2-acetamido pentamethylenesulfonium trifluoroacetate. The synthetic preparation for each of these individual compounds is shown in the Examples.

The N-hydroxymethyl compounds may be derivatized or prepared directly with the particular acid or hydroxyl replacing group in the reaction mixture during the N-substitution of the α-substituted acetamide or by using a formaldehyde derivative such as α-chloromethyl methoxyethyl ether.

The activation of the polystyrene will occur under mild conditions in a solvent which neither dissolves nor swells the polystyrene While the preferred solvent is TMS, other solvents which are less efficient may find use, such as acetonitrile, nitromethane, and DMSO (dimethyl sulfoxide).

The reaction will be carried out in the presence of a strong acid, particularly a protonic acid, preferably an organic acid, such as trifluoroacetic acid, trifluoromethanesulfonic acid, methanesulfonic acid, sulfuric acid, phosphoric acid, or hydrogen fluoride. The concentration of the acid will generally range from about 0.1 to 2 M. The reaction will normally be carried out in the substantial absence of atmospheric moisture, which can be achieved by covering the reaction mixture, providing for an inert atmosphere, or the like.

The polystyrene surface is contacted with the N-(Y-methyl) acetamide compound within a temperature and time range suitable for activating the surface of the substrate. Generally, the temperature will range from about −5° C. to about 60° C., preferably about 0° to about 30° C., and the activation time is from about 5 min to about 48 h, usually from about 2 to about 8 h. The concentration of the N-(Y-methyl) acetamide compound is typically between about 0.01 to 2 M, usually between about 0.05 to 0.5 M. For most applications, the use of at least about 0.05, usually 0.1 ml of reaction solution per square centimeter of solid substrate surface area is sufficient to provide for the desired level of activation by reaction of electrophilic groups on the surface of the substrate.

Before the conjugation of the macromolecule, the surface of the substrate may be freed of any unreacted N-(Y-methyl) acetamide compound by washing with a buffer and/or water. The particular material employed for the washing step is not critical to the invention, and is chosen for convenience, so long as the conditions do not affect the substitutable group of the amide. Substitution of the substitutable group may be conducted immediately after activation, or at some interval of time, since the surface is stable when stored in an inert environment After activation of the polystyrene surface, the linking group is formed by replacement of the halide or pseudohalide present on the surface Different groups may be employed for substitution of the halogen or pseudohalogen, including thiol, oxy or amino, preferably thiol. The conditions for the nucleophilic substitution will be substantially conventional, generally employing a non-dissolving, non-swelling solvent media such as water and aqueous buffers, TMS, DMSO, aliphatic alcohols, at a temperature in the range of −5° to 60° C., usually 0° to 30° C., usually in the presence of base, usually at a pH in the range of about 8 to 14. The time for the reaction may vary from about 5 min to 12 h. The substituting group will provide for an available amino or hydroxyl group for bonding of the next molecule The compounds employed will generally be from about 2 to 8 carbon atoms, more usually from 2 to 6 carbon atoms, and preferably from 2 to 4 carbon atoms, more preferably 2 carbon atoms. For the most part, the compounds will be aliphatic and aliphatically saturated. During the reaction, the amino group may be protected or unprotected, depending upon the nature of the substituting group. Protective groups may include benzyloxycarbonyl, acetyl, butyloxycarbonyl, or the like.

Illustrative compounds include aminoethylmercaptan, mercaptoethanol, ethylene diamine, other alkylene diamines and triamines.

In some instances, it may be desirable to further extend the linking group by providing for an acid, base, or hydrazine cleavable benzyl alcohol functionality for preparing the oligopeptide. Various derivatives of benzyl alcohol may be employed for reacting with the available amino group, where the extending molecule bonded to the amino group will have at least 7 carbon atoms and not more than about 14 carbon atoms, usually not more than about 12 carbon atoms. The benzyl alcohol which provides for an ester linkage allows for removal and isolation of the oligopeptide which is produced. In contrast, where it is intended that the oligopeptide remain bonded to the polystyrene solid support, the stabler amide linker will be preferred.

For the most part, the oligopeptides which are produced will be comprised solely of amino acids either the natural carrying L-amino acid or the normally, unnaturally occurring D-amino acid. However, molecules other than amino acids may be included internal to the chain or as the terminal group, as desired Unnatural amino acids may also be employed, such as p-aminobenzoic acid, 4-aminobutyric acid, or the like. In referring to amino acid, it is intended to use the term generically, in that the molecule has a carboxyl functionality and an amino functionality.

For the purposes of the subject invention, it is desirable that the transparency of the polystyrene be retained. Therefore, a process has been devised which is efficient, provides a high level of fidelity, uses generally available reagents, and can be readily reproduced. In the system, solvents and reagents which would react with or act on the polystyrene are avoided. The amino acid reactants are selected for solubility in the solvents which are employed. The amino acids will usually have the terminal amino group protected, employing conventional protective groups. For the subject invention, the fluorenylmethoxycarbonyl has been found to be effective and is preferred. Other groups may find use as appropriate.

The monomers which are employed will be activated so as to be able to react with the functional group to which they are to be attached For the most part, carboxyl groups will be involved which will be activated in a variety of ways, particularly as anhydrides or activated esters The anhydrides will, for the most part, be symmetrical anhydrides, although in some situations, mixed anhydrides may also be employed. Mixed anhydrides will usually involve ester carbonate anhydrides of the monomer. Alternatively, activated esters may be employed, where a variety of alcohols or phenols may be employed In many instances, different esterifying agents will be employed, depending upon the particular monomer. Esterifying agents of particular interest include pentafluorophenol, 1-hydroxybenzotriazole, 3,4-dihydro-3-hydroxy-4-oxo-1,2,3-benzotriazine, 4-nitrophenol, 2,4-dinitrophenol, N-hydroxysuccinimide, and pentachlorophenol.

The activated monomer will be added to the linking group or growing chain in a non-hazing solvent. Desirably, a combination of tetramethylene sulfone and dimethyl sulfoxide will be employed as the solvent, generally in the ratio of about 1:3–3:1, preferably about 1:1. The time for the reaction will vary, generally ranging from about at least 0.5h and not more than about 3h, generally ranging from about 1 to 2h. The concentration of the monomer will generally be in the range of about 0.05 to 1.0M. Desirably, room temperature is employed, although lower or higher temperatures may be employed, generally in the range of about 4-°60° C.

After completion of the reaction, the solution may be removed and any unreacted amino groups capped. For capping, acetylating agents may be employed, conveniently 1-acetylimidazole. A solution of the capping agent in 1:1 TMS/DMSO will be employed for at least about 0.5h and generally not exceeding about 3h, usually not exceeding about 2h, 1h generally being satisfactory. The concentration of the capping agent will usually be at least about 0.5M, and not more than about 1.5M, more usually not more than about 1M.

After completion of capping, the protective groups will be removed. Generally, heterocyclic amines will be employed, where the nitrogen is a member of the ring, particularly rings of from 5 to 6 carbon atoms and desirably having an hydroxyl group. Preferred is 4-hydroxypiperidine. The concentration of the deprotecting amine will generally be in the range of about 0.1 to 1.0M and deprotection will generally be carried out at about room temperature, although any temperature from 10° to 30° C. may be employed The solvent will be the same solvent as used previously.

The deprotecting solution is then removed and the cycle repeated by adding the next monomer. The process will usually be carried out for at least 5 cycles and may be carried out for 25 cycles or more. It is understood that the yield will diminish with each cycle, although the subject method provides for high yields with peptides not exceeding 15 monomers.

At the completion of the synthesis, the terminal amino group will be deprotected as described above, followed by deprotection of the side chain functionalities. Since the side chain functionalities will vary depending upon the particular monomer, deprotection conditions will be employed which are sufficient for the side group protecting functionality requiring the most rigorous conditions. Where less rigorous conditions suffice, the less rigorous conditions may be employed. For the most part, it has been found that various acidic treatments may be employed, conveniently 95% trifluoroacetic acid in water for at least about 120 min., preferably at least 180 min. at room temperature. Where the peptide is linked to the solid support by an ester link, the acid hydrolysis also releases the peptide from the support.

The subject invention provides minimum purities of at least about 70% for oligopeptides in excess of about 10 amino acids. In addition, per well of a multiwell plate, one nanomole or more may be obtained.

The peptides as bound to the support may find a wide variety of uses. Conveniently, the peptides may be prepared as ligands for use in diagnostic assays. Thus, the peptide will be cross reactive with a ligand of interest, so that enzyme-antibody conjugates may bind to the oligopeptide on the support in competition with analyte in the medium. Conventional assays, such ELISA assays may be employed with advantage. See, for example, U.S. Pat. No. 3,850,752. Thus, plates may be preprepared which may be used directly in ELISA assays for ligands of interest.

In addition, the oligopeptide containing plates may be used for screening receptors, isolating cells, receptors, antibodies or the like, which specifically bind to the oligopeptides, investigating structural conformation of such binding molecules by virtue of varying the oligopeptide sequence, and the like.

The following examples are offered by way of illustration and not by way of limitation.

EXPERIMENTAL

Dynatech/polystyrene microtiter plates were functionalized with functionalized with N-hydroxymethyl 2-bromoacetamide (BA) as follows. A 0.2M solution of N-hydroxymethyl 2-bromoacetamide in tetramethylenesulfone (TMS) was combined in a 1:1 ratio with a 2M trifluoromethylsulfonic acid (TMSA) and the reaction solution was immediately added to the microtiter plate wells. The reaction solution was left in contact with the polystyrene surface for 5h at room temperature, washed with water until odorless, and air dried at room temperature overnight. The surfaces were stable for at least two weeks in a dry, light free environment. At least 0.1ml of reaction solution per square centimeter of polystyrene surface was used.

POLYSTYRENE ACTIVATION (AEA)

The BA activated surface was reacted with 2-aminoethanethiol (Aldrich) to provide the Aminoethylacetamide (AEA) primary amine surface for peptide synthesis, using a 0.15M solution in 1:1 v/v TMS/DMSO or 0.25M $Na_2CO_3$ in $H_2O$.

The conversion of the BA surface to the AEA surface was tested by treating AEA wells with 5 mM bromophenol blue (BPB) in DMSO. The dye forms an ion pair with amine groups. The dye can be released using 50 mM carbonate pH=9.2 containing 10% DMSO. The soluble dye absorbance at 570nm (subtracting background at 650nm) is measured with an ELISA plate reader. This technique was employed frequently to qualitatively monitor the coupling and deprotection steps of solid phase multiple peptide synthesis (SPMPS).

The data in Table 1 demonstrates the application of BPB/amine binding to study the conversion of the BA surface to the AEA surface. The transformation was also validated by ESCA. There was a low level of nonspecific dye staining for the polystyrene and BA surfaces.

TABLE 1

BROMOPHENOL BLUE DYE BINDING TO AN AEA PLATE

| Polystyrene | BA | AEA Surface |
|---|---|---|
| 0.002 ± .001 | 0.004 ± .001 | 0.767 ± .084 |

PEPTIDE SYNTHESIS (Stability)

The stability of the peptide synthesis surface to methyl sulfoxide (DMSO) and a 1:1 mixture of DMSO and tetramethylene sulfone (TMS) was tested. The Fmoc-amino acid-OPfp esters were not completely soluble in TMS alone, but quite soluble in DMSO. (Fmoc=fluorenylmethoxycarbonyl, OPfp=pentaflurophenyl) A 1:1 mixture of TMS:DMSO was employed as solvent. The solvent system was compatible with automated pipetter systems, (i.e., nondestructive to the hardware).

A stability study was performed coupling alanine to the SPMPS surface and carrying out 15 cycles of peptide synthesis, excluding the use of Fmoc-amino acid-OPfp esters (i.e., just solvent) due to the expense of the reagents. Because analysis for alanine was required at the end of 5, 10, and 15 cycles, the acid cleavable linker 4-hydroxymethylphenoxyacetic acid was coupled to the AEA plate via its pentafluorophenyl ester (see below) and Fmoc-alanine symmetric anhydride was coupled to the linker plate by conventional methods using 0.1M diisopropyl carbodiimide, 0.1M Fmoc-alanine, 0.05M dimethylamino-pyridine, and the reaction allowed to proceed for 90 min. The synthesis cycles were then performed by the Beckman Biomek 1000 automated pipetter.

After 5, 10 and 15 cycles the wells were treated with TFA/H$_2$O (95:5) to release the alanine, which was quantitated by amino acid analysis. The AEA +linker +alanine is stable to TMS/DMSO for at least 15 cycles. DMSO alone caused a decrease in recovered alanine by 67% over 15 cycles.

After cleaving the alanine from the peptide synthesis surface, water was added to the wells and the plate was read in an ELISA reader at 570nm. The absorbance data at 0 (polystyrene), 5, 10, and 15 cycles of SPMPS are shown in Table 2. The peptide synthesis surface showed no increase in optical density. If hazing had occurred the optical density would have increased with the number of SPMPS cycles.

TABLE 2

HAZING OF THE SPMPS SURFACE DETERMINED BY OPTICAL DENSITY

| SPMPS Cycles | A570 |
|---|---|
| 0 CYCLES | 0.046 |
| 5 CYCLES | 0.046 |
| 10 CYCLES | 0.047 |
| 15 CYCLES | 0.047 |

PEPTIDE SYNTHESIS (Capping)

When it was necessary to cap uncoupled free amino groups, 1-acetylimidazole was used. Capping was performed with 0.5M acetylimidozole in 1:1 TMS/DMSO for 1 h at room temperature.

The decrease in BPB binding was used to indicate capping efficiency. Since the capping reagent is sensitive to water, reaction time was kept to 1.0 hour at room temperature. From this data, a capping concentration of 0.8M was selected with a reaction time of 1.0 hour.

PEPTIDE SYNTHESIS (Deprotection)

The time dependence of the deprotection step was studied using an AEA plate coupled with Fmoc-glycine. The deprotection of the Fmoc group by 4-hydroxypiperidine was monitored over time using the bromophenol blue test at regular intervals. Maximum dye binding (and thus maximum deprotection of the amine group) was reached at approximately 6 minutes. For SPMPS, deprotection was allowed to go for 20 minutes to insure a complete deprotection step.

PEPTIDE SYNTHESIS (Coupling)

The time dependence of the coupling reaction to an AEA plate with several Fmoc-amino acid pentafluorophenyl esters was studied. Coupling was performed with 0.1M Fmoc-amino acid - OPfp in 1:1 TMS/DMSO for 90 min. In cases of double coupling, after aspiration of the reaction medium, the step is repeated. (see Table 3). The coupling completeness was measured using the bromophenol blue test: a low BPB reading being indicative of high coupling efficiency. After the coupling reaction, the wells were capped and tested with BPB again. To gain insight into the efficiency of the process, the coupled amino acid was deprotected and tested with dye for comparison with the original AEA plate. The comparison only serves as a guide to efficiency, which was quite good for all couplings investigated.

TABLE 3

BPB BINDING TO ASSESS COUPLING EFFICIENCY TO AEA SURFACE

| AMINO ACID COUPLED | AEA WELL | COUPLED FMOC—AA | CAPPED FREE AMINE | DEPROTECTED FMOC—AA |
|---|---|---|---|---|
| FMOC—ARG(PMC)Obt* 90 MINUTES | .427 | .017 | .008 | .414 |
| FMOC—ARG(PMC)Obt* 180 MINUTES | .368 | .013 | .008 | .451 |
| FMOC—PRO—OPfp 90 MINUTES | .425 | .091 | .017 | .325 |
| FMOC—PRO—OPfp 180 MINUTES | .477 | .041 | .012 | .446 |
| FMOC—LYS(BOC)—OPfp 90 MINUTES | .474 | .024 | .012 | .512 |

TABLE 3-continued

| BPB BINDING TO ASSESS COUPLING EFFICIENCY TO AEA SURFACE | | | | |
|---|---|---|---|---|
| AMINO ACID COUPLED | AEA WELL | COUPLED FMOC—AA | CAPPED FREE AMINE | DEPROTECTED FMOC—AA |
| FMOC—LYS(BOC)—OPfp 180 MINUTES | .520 | .015 | .011 | .602 |
| FMOC—PHE—OPfp 90 MINUTES | .490 | .035 | .016 | .513 |
| FMOC—PHE—OPfp 180 MINUTES | .549 | .019 | .013 | .607 |
| FMOC—TRP—OPfp 90 MINUTES | .496 | .053 | .017 | .485 |
| FMOC—TRP—OPfp 180 MINUTES | .497 | .038 | .013 | .529 |

*Obt is 1-hydroxybenzotriazole active ester

PEPTIDE SYNTHESIS (Coupling) cont.

Several Fmoc-amino acid active esters were tested for their ability to undergo a relatively unhindered coupling to a glycine residue coupled to AEA. The data in Table 4 reveal that coupling (monitored by reduction in BPB absorbance) is complete after the first coupling of 90 minutes, with a small improvement after the second coupling. The Fmoc-protected dipeptides were deprotected with 4-hydroxypiperidine and tested with BPB for to the starting AEA wells. The qualitative results gleaned by comparing the AEA starting wells to the deprotected Fmoc-AA (amino acid) wells indicated a high overall efficiency for coupling two residues. In fact, BPB binding is actually higher for the dipeptides than the starting AEA wells.

TABLE 4

| BPB BINDING TO ASSESS COUPLING EFFICIENCY TO GLYCINE COUPLED AEA | | | | |
|---|---|---|---|---|
| AMINO ACID COUPLED | | COUPLED FMOC—AA—GLY | DEPROTECTED DIPEPTIDE | STARTING AEA WELL |
| FMOC—LYS(BOC)—OPfp | 1× | .005 | .484 | .399 |
| FMOC—LYS(BOC)—OPfp | 2× | .005 | .471 | .386 |
| FMOC—PHE—OPfp | 1× | .008 | .406 | .383 |
| FMOC—PHE—OPfp | 2× | .007 | .412 | .398 |
| FMOC—PRO—OPfp | 1× | .010 | .415 | .384 |
| FMOC—PRO—OPfp | 2× | .008 | .432 | .393 |
| FMOC—SER*—ODhbt** | 1× | .004 | .463 | .406 |
| FMOC—SER*—ODhbt** | 2× | .004 | .458 | .403 |
| FMOC—TYR*—OPfp | 1× | .008 | .500 | .432 |
| FMOC—TYR*—OPfp | 2× | .006 | .531 | .471 |

*Side-chain protected as t-butyl ether
*ODhbt is 3,4-dihydro-3-hydroxy-4-oxo-1,2,3-benzotriazine active ester.

PEPTIDE SYNTHESIS (Coupling) cont.

The same group of Fmoc-amino acid-active esters used in the glycine coupling study (Table 5) were tested for their coupling with a more hindered residue: isoleucine previously coupled to AEA. The results in Table 5 point to the necessity for two coupling cycles with more hindered condensations. This is evidenced by the difference between the first and second couplings of the Phe, Pro, and Tyr residues. Again, qualitative comparison of the BPB-dipeptide binding with the starting AEA absorbance would seem to indicate very efficient overall coupling, even with these very hindered coupling reactions.

TABLE 5

| BPB BINDING TO ASSESS COUPLING EFFICIENCY TO ISOLEUCINE COUPLED AEA | | | | |
|---|---|---|---|---|
| AMINO ACID COUPLED | | COUPLED FMOC—AA—ILE | DEPROTECTED DIPEPTIDE | STARTING AEA WELL |
| FMOC—LYS(BOC)—OPfp | 1× | .006 | .427 | .402 |
| FMOC—LYS(BOC)—OPfp | 2× | .005 | .409 | .395 |
| FMOC—PHE—OPfp | 1× | .012 | .331 | .383 |
| FMOC—PHE—OPfp | 2× | .006 | .338 | .381 |
| FMOC—PRO—OPfp | 1× | .015 | .330 | .379 |
| FMOC—PRO—OPfp | 2× | .006 | .352 | .399 |
| FMOC—SER*—ODhbt** | 1× | .004 | .422 | .400 |
| FMOC—SER*—ODhbt** | 2× | .003 | .442 | .423 |
| FMOC—TYR*—OPfp | 1× | .015 | .396 | .426 |
| FMOC—TYR*—OPfp | 2× | .006 | .523 | .498 |

*Side-chain protected as t-butyl ether
**ODhbt is 3,4-dihydro-3-hydroxy-4-oxo-1,2,3-benzotriazine active ester.

PEPTIDE SYNTHESIS (Side-Chain Deprotection)

In both the direct and linker methods, the Fmoc group of the N-terminal residue is removed before side-chain deprotection. The side-chain protecting groups (t-butyl esters, t-butyl ethers, butoxycarbonyl (Boc) and 2,2,5,7,8-(pentamethylchroman-6-sulphonyl) (PMC) are then cleaved by acid treatment.

A time course study of side-chain deprotection is shown in Table 6. Different acid/water combinations were studied for their ability to effect the deprotection of Lys(Boc) and Arg(PMC) side chain protecting groups, since these side-chains were most relevant to the synthesis of a-MSH.

TABLE 6

BPB BINDING TO DEPROTECTED BASIC RESIDUES WITH TIME

| AMINO ACID | T = 0 | T = 5 | T = 15 | T = 30 | T = 60 | T = 90 | T = 180 min |
|---|---|---|---|---|---|---|---|
| FMOC—LYS (BOC 90% TFA/ WATER | .022 | 1.146 | 1.207 | 1.361 | 0.953 | — | — |
| FMOC—ARG (PMC) 90% TFA/ WATER | .022 | 0.040 | 0.064 | 0.071 | 0.128 | — | — |
| FMOC—ARG (PMC) 95% TFA/ WATER | .022 | — | — | — | — | 0.146 | 0.286 |
| FMOC—ARG (PMC) 95% TFA/ WATER + 0.5M TFMSA | .022 | — | — | — | — | — | 0.282 |
| FMOC—ARG (PMC) 95% TFA/ WATER + 1.0M TFMSA | 0.22 | — | — | — | — | — | 0.306 |

PEPTIDE SYNTHESIS (Side-Chain Deprotection)

The Boc protecting group reaches the maximum dye binding within the first 30 minutes of the reaction with 95% TFA/H$_2$O. The PMC group does not reach a maximum until 180 minutes reaction with 95% TFA/H$_2$O. The conclusion from this study was that 95:5 TFA:H$_2$O for 3h at room temperature was sufficient to remove very acid labile groups like Boc and t-butyl esters/ethers, as well as less susceptible groups like PMC.

In direct SPMPS the peptide side chain groups were deprotected with TFA/H$_2$O while the peptide remained covalently bonded to the plate. At this point, the peptide was ready to be analyzed by a method such as an ELISA.

In linker SPMPS (linker is the hydroxymethylphenoxyacetic acid), the peptide side-chain groups were deprotected and the peptide simultaneously cleaved from the plate by TFA/H$_2$O. A sequence analysis could be performed directly on the peptide. In addition, amino acid analysis could be performed after hydrolyzing the deprotected peptide with 6N HCl at 110° C. for 24 hours.

AMINO ACID ANALYSIS (α-MSH)

Amino acid analysis was done on alpha-melanocyte stimulating hormone (α-MSH) after synthesis using the linker methodology. The data is shown below in Table 7.

TABLE 7

AMINO ACID ANALYSIS DATA FOR a-MSH

| AA | THEORY | a-MSH #1 | a-MSH #2 | a-MSH #3 |
|---|---|---|---|---|
| Val = V | 1.000 | 0.860 (9138) | 0.878 (4725) | 9.946 (5565) |
| Pro = P | 1.000 | 1.000 (10627) | 1.000 (5381) | 1.000 (5877) |
| Lys = K | 1.000 | 0.606 (6436) | 0.531 (2857) | 0.562 (3306) |
| Gly = G | 1.000 | 0.380 (4035) | 0.377 (2027) | 0.391 (2300) |
| Trp = W | 1.000 | — | — | — |

TABLE 7-continued

AMINO ACID ANALYSIS DATA FOR a-MSH

| AA | THEORY | a-MSH #1 | a-MSH #2 | a-MSH #3 |
|---|---|---|---|---|
| Arg = R | 1.000 | 0.251 (2667) | 0.239 (1288) | 0.221 (1302) |
| Phe = F | 1.000 | 0.236 (2794) | 0.231 (1244) | 0.230 (1355) |
| His = H | 1.000 | 0.296 (3148) | 0.257 (1389) | 0.260 (1529) |
| Glu = E | 1.000 | 0.264 (2806) | 0.230 (1240) | 0.232 (1366) |
| Met = M | 1.000 | 0.100 (1048) | 0.103 (555) | 0.015 (91) |
| Ser = S | 2.000 | 0.555 (5900) | 0.632 (3400) | 0.577 (3389) |
| Tyr = Y | 1.000 | 0.176 (1872) | 0.186 (1000) | 0.140 (823) |

( ) = Peak area from amino acid analysis
Note:
a-MSH #1 = a-MSH synthesized with capping of the first 7 residues.
a-MSH #2 and #3 = a-MSH synthesized without.

The data indicates no significant difference between the capped and the non-capped syntheses. Analysis for Trp is not possible due to degradation in the 6M HCl acid hydrolysis. Methionine was low, probably, because of oxidation during acid hydrolysis.

The conclusions from this study are that the proper residues are present in amounts indicating a successful synthesis. This was confirmed by the sequence analysis of α-MSH (see below). The early residues are in higher amounts than the later residues (a 40% decrease in detected lysine and a further 33% decrease in detected glycine was noted in all three syntheses).

AMINO ACID ANALYSIS (Leu-5-Enkephalin)

The amino acid analysis of the peptide Leu-5-enkephalin is shown below in Table 8. The ratios for leucine, tyrosine and pheenylalanine are near theory. However, the ratio for glycine was found to be significantly higher than theory.

TABLE 8

SEQUENCY ANALYSIS OF LEU-5-ENKEPHALIN

| Amino Acid | Theo. Value | Raw Data | Leu-Enk |
|---|---|---|---|
| Leu = L | 1.000 | 3143 | 0.643 |
| Phe = F | 1.000 | 4891 | 1.000 |
| Gly = G | 2.000 | 155488 | 3.167 |
| Tyr = Y | 1.000 | 4585 | 0.937 |

In the Leu-5-enkephalin work, the possible steric requirement for some of the peptide chains is avoided. This results in much more satisfactory amino acid analysis values. Glycine is 50% higher than theory, which is the result of double couplings occurring or contamination. Double coupling occurs if residual 4-hydroxypiperdine is present. This is avoided by providing extra washes to the Biomek deprotection subroutine.

SEQUENCE ANALYSIS (α-MSH)

In addition to the amino acid analysis data for α-MSH #1 (Table 7), sequence analysis was performed, and the data is shown in Table 10. The sequence analysis by repetitive Edman degradation on an Applied Biosystems 420A Derivatizer gave the correct phenylthiohydantoin (PTH) amino acid for all residues in α-MSH (with the exception of Trp) in greater than 70% yield of the theoretical. Quantitation of the data showed that each well contains approximately 1 nanomole of completed peptide, based on the amount of N-terminal serine detected. An amount of peptide in the picomole range is considered necessary for ELISA detection, so clearly the subject invention provides adequate amounts of peptide synthesized in each well.

In nearly all cases, the main PTH amino acid was detected along with a small percentage of the PTH amino acid corresponding to the next residue in the sequence. This "foreshadowing" is most likely a machine artifact, or a failure to completely couple the last serine residue in α-MSH. In either case, it suggests that 70% is the minimum purity of the synthesized peptide.

Tryptophan was not detected, although it theoretically should have been present. The primary residue detected where tryptophan should have been found (cycle 9) was glycine, the "foreshadow" residue of tryptophan. This implies that Trp is destroyed by the global deprotection conditions, emphasizing the strong need to develop global deprotection conditions which include the addition of scavengers.

TABLE 9

SEQUENCE ANALYSIS DATA FOR a-MSH

| Edman Cycle | Theor. PTH Amino Acid | Detected PTH Amino Acid(s) | Yield Picomoles* | % Correct Sequence** |
|---|---|---|---|---|
| 1 | Ser = S | S (G) (Y) | 3147 (613) (470) | 74 |
| 2 | Tyr = Y | Y (L) | 4206 (560) | 88 |
| 3 | Ser = S | S (M) | 3005 (219) | 93 |
| 4 | Met = M | M (E) | 5458 (190) | 97 |
| 5 | Glu = E | E | 2733 | 100 |
| 6 | His = H | H (F) | 753 (280) | 73 |
| 7 | Phe = F | F (R) | 2170 (610) | 78 |
| 8 | Arg = R | R (G) | 1465 (340) | 81 |
| 9 | Trp = W | G (K) | 1022 (240) | |
| 10 | Gly = G | G (K) | 1703 (690) | 71 |
| 11 | Lys = K | K (P) | 1258 (262) | 83 |
| 12 | Pro = P | P (V) | 393 (90) | 81 |
| 13 | Val = V | V | 145 | 100 |

*Data is based on 8 synthesis wells and ½ dilution of the sample. Thus the amount of peptide can be determined by the following: last synthesized residue (serine) equals 3,147 picomoles multiplied by 1 yields approximately 1 nanomole per well.
**All PTH amino acids with 3% or greater of the total absorbance for all peaks detected are listed. All other peaks were considered to be background.

The ELISA (Enzyme Linked ImmunoSorbent Assay) represents one of the most useful potential applications of the SPMPS technique. An ELISA was accomplished in SPMPS by direct synthesis of the peptide on the AEA surface, followed by acid deprotection of the side-chain protecting groups. The wells were then blocked with bovine serum albumin to reduce nonspecific binding. Rabbit anti-(α-MSH) or rabbit anti-Leu-5-enkephalin was added to the wells, and antibodies recognizing the peptide were bound. Detection of the bound rabbit antibodies binding was accomplished by incubation with alkaline phosphatase (AP) conjugated to goat anti-rabbit IgG, followed by washing to remove excess conjugate, and addition of p-nitrophenyl phosphate, a substrate of AP. The AP turned over the substrate to generate p-nitrophenolate, which was spectrophotometrically detected at 405nm in an ELISA plate reader. Dilutions of rabbit IgG passively adsorbed to a polystyrene microtiter plate were detected with different dilutions of the conjugate. A final dilution of 1:3500 was found to be optimum. Control wells (no rabbit IgG) showed low background binding (absorbance at 405nm-650nm <0.040). This validated the use of this conjugate for the SPMPS ELISA studies.

An ELISA was run on the pentapeptide (Y-G-G-F-L) Leu-5-enkephalin peptide. It was compared to several other surfaces for binding to rabbit anti-(Leu-5-enkephalin): N-terminal Fmoc enkephalin (FMOC-ENK), Liner-synthesized Leu-5-enkephalin after acid release of peptide (L-ENK), a tripeptide Phe-Gly-Tyr (F-G-Y), and N-terminal acetylated Leu-5-enkephalin (ENK-AC). The data below showed that the strongest immunoreactivity was seen with ENK and ENK-AC, as expected. There was some cross-reactivity with the tripeptide F-G-Y. No immunoreactivity was seen for the FMOC-ENK peptide. The slight immunoreactivity observed for the L-ENK wells may indicate that some peptide remains bound to the wells after the acid deprotection.

The following is a flow chart of the process:

| Operation | Reactant | Solvent | Cycles | Time Hours |
|---|---|---|---|---|
| WASH* | SPMPS SURFACE | TMS/DMSO | 3 | — |
| Couple | FMOC-AMINO | TMS/DMSO | — | 1.5 |
| Recouple | FMOC-AMINO ACID PFP ESTER | TMS/DMSO | — | 1.5 |
| WASH | SPMPS SURFACE | TMS/DMSO | 3 | — |
| CAPPING** | N-ACETYL-IMIDAZOLE | TMS/DMSO | — | 1.0 |
| WASH | SPMPS SURFACE | TMS/DMSO | 3 | — |
| DEPROTECTION | 4-HYDROXY-PIPERIDINE | TMS/DMSO | 2 | — |
| WASH | SPMPS SURFACE | TMS/DMSO | 2 | — |

*Start at first wash for all cycles
**Capping was done for "hard" to couple sequences only; BPB test was done after recouple, after capping and/or after deprotection It is evident from the above results that the subject methodology provides for a convenient rapid method for producing relatively large amounts of oligopeptides with high fidelity. Thus, devices can be provided, where a surface has a specific sequence or a plurality of different, either related or unrelated sequences, for use in assays, research, and the like. In addition, oligopeptides may be prepared which are easily freed from this support and may find use as drugs, as ligands in competitive assays, and the like. The method allows for optically transparent solid supports, so that the course of the reaction may be observed and where problems occur, the reaction may be stopped. Furthermore, where assays are being carried out, the transparent support allows for light transmission, so that spectrophotometers may be used effectively. Thus, the methodology permits carrying out of fluorescent or enzyme assays, where the label requires detection of light.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fabricated polystyrene article characterized by:
   being optically clear;
   being functionalized at high density at an activated polystyrene support article surface with linking groups terminating in a primary amino or hydroxy group, and
   having linked to said terminating amino or hydroxy group (a) an amino acid the amino group thereof optionally coupled to a protecting group used for peptide synthesis or (b) an oligopeptide, wherein said oligopeptide is substantially uniform in composition and the N-terminal amino group of said oligopeptide is optionally coupled to a protecting group used for peptide synthesis.

2. An article according to claim 1, wherein said article is a multiwell plate and is functionalized in a well of said multiwell plate.

3. An article according to claim 9 wherein said polystyrene is activated with a group which comprises a methyleneaminoacetyl group.

4. An article according to claim 3 wherein said linking group comprises a thioalkyleneamine group bonded through the thio to said acetyl group of said activating group.

5. An article according to claims 1 or 4 wherein said linking group is extended with a group comprising a benzyl alcohol group bonded to said terminating group.

6. An article according to claim 2 wherein all of the linking groups in a well have either all amino or all hydroxy groups in a well.

7. An article according to claim 1, wherein said article is a container.

8. A polystyrene bead characterized by:
being optically clear;
being functionalized at high density at an activated polystyrene bead surface with linking groups terminating in primary amino or hydroxy group; and
having linked to said terminating amino or hydroxy group (a) an amino acid the amino group thereof optionally coupled to a protecting group used for peptide synthesis or (b) an oligopeptide, wherein said oligopeptide is substantially uniform in composition and the N-terminal amino group of said oligopeptide is optionally coupled to a protecting group used for peptide synthesis.

9. An article according to claim 1 wherein the protecting group is fluorenylmethoxycarbonyl.

10. Beads according to claim 1 wherein the protecting group is fluorenylmethoxycarbonyl.

11. A fabricated polystyrene article characterized by:
being optically clear;
being functionalized at high density at an activated polystyrene support article surface with linkage groups terminating in a primary amino or hydroxy group; and
having linked to said terminating amino or hydroxy group an oligopeptide, wherein said oligopeptide is substantially uniform in composition.

12. An article according to claim 1 or 3 wherein said linking group terminates in an aliphatic primary amine, an aliphatic primary hydroxyl, or a benzyl alcohol group.

13. An article according to claim 1 said linking group is extended by a group comprising a benzyl alcohol group.

14. An article according to claim 5 wherein said benzyl alcohol group is hydroxymethylphenoxyacetic acid.

15. An article according to claim 1 or 3 wherein said polystyrene is characterized by having fewer than about 0.1 percent crosslinks.

16. An article according to claim 1 or 3 wherein said terminating group is a primary amino group.

17. An article according to claim 1 or 3 wherein said terminating group is a hydroxy group.

18. An article according to claim 1 or 3 wherein said polystyrene is activated with a group which comprises a methyleneaminoacetyl group.

19. An article according to claim 2 wherein said activating group comprises a methyleneaminoacetyl group, said linking group is a thioalkyleneamine or hydroxy group optionally further extended with a group comprising a benzyl alcohol group bonded to said amino or hydroxy functionality.

20. A bead according to claim 8 wherein said polystyrene is activated with a group which comprises a methyleneaminoacetyl group.

21. A bead according to claim 8 wherein said linking group comprises a thioalkyleneamine group bonded through the thio to said activating group.

22. A bead according to claim 21 wherein said linking group is extended with a group comprising a benzyl alcohol group bonded to said terminating group.

23. A bead according to claim 8 wherein said terminating group is a primary amino group.

24. A bead according to claim 8 wherein said terminating group is a hydroxy group.

25. A bead according to claim 8 wherein said polystyrene is characterized by fewer than about 0.1 percent crosslinks.

26. A bead according to claim 8 wherein said activating group comprises a methyleneaminoacetyl group, said linking group is a thioalkyleneamine or hydroxy group optionally further extended with a group comprising a benzyl alcohol group bonded to said amino or hydroxy functionality.

* * * * *